United States Patent
Parker et al.

(10) Patent No.: US 11,998,421 B2
(45) Date of Patent: Jun. 4, 2024

(54) ORTHODONTIC MODELING FILLER MATERIAL AND METHOD

(71) Applicants: Kammy Parker, Waco, TX (US); Gina Parker, Waco, TX (US)

(72) Inventors: Kammy Parker, Waco, TX (US); Gina Parker, Waco, TX (US)

(*) Notice: Subject to any disclaimer, the term of this patent is extended or adjusted under 35 U.S.C. 154(b) by 379 days.

(21) Appl. No.: 17/246,857

(22) Filed: May 3, 2021

(65) Prior Publication Data
US 2021/0346130 A1 Nov. 11, 2021

Related U.S. Application Data

(60) Provisional application No. 63/020,515, filed on May 5, 2020.

(51) Int. Cl.
*A61C 9/00* (2006.01)
*A61C 13/34* (2006.01)
*A61K 6/60* (2020.01)
*A61K 6/70* (2020.01)
*A61K 6/90* (2020.01)

(52) U.S. Cl.
CPC ............ *A61C 9/0006* (2013.01); *A61C 13/34* (2013.01); *A61K 6/60* (2020.01); *A61K 6/70* (2020.01); *A61K 6/90* (2020.01); *A61C 2201/00* (2013.01)

(58) Field of Classification Search
CPC ........................................................ A61K 6/90
See application file for complete search history.

(56) References Cited

U.S. PATENT DOCUMENTS

| | | | | |
|---|---|---|---|---|
| 5,980,880 A | * | 11/1999 | Love | A61L 9/01 424/78.05 |
| 2002/0187456 A1 | * | 12/2002 | Craig | A61K 6/90 433/48 |
| 2005/0048442 A1 | * | 3/2005 | Parker | A61C 9/00 433/213 |

* cited by examiner

*Primary Examiner* — Michael F Pepitone
(74) *Attorney, Agent, or Firm* — Naman, Howell, Smith & Lee, PLLC; John A. Powell

(57) ABSTRACT

An improved dough-like filler material for use in dental and orthodontic modelling and the manufacturing methods that may be used to produce such improved dough-like filler material.

4 Claims, 8 Drawing Sheets

ORTHODONTIC MODELING FILLER MATERIAL AND METHOD

PRIORITY CLAIM

This application claims priority to U.S. Provisional Application No. 63/020,515 filed on May 5, 2020, which is hereby incorporated by reference.

TECHNICAL FIELD OF THE INVENTION

The present invention relates to orthodontic modeling methods and materials.

BACKGROUND ART OF THE INVENTION

Dental models or "impressions" are made for many dental and orthodontic procedures. Models are made first by producing a rough, negative topological impression. This is taken with the assistance of a standard perforated metal or plastic tray, wherein for the impression material alginate, palate, etc. are used. Then the topological impression is used to form a cast using hard plaster, which produces a positive topological model, which, in turn, reflects the rough topology found in the mouth or on the biting surfaces of the patient, i.e. existing or absent teeth, the shape of the jaw crest and the mucous membranes, irregularities, etc.

For certain procedures, a number of additional steps are involved, and include the creation of a negative topological tray or "functional tray", a precise topological or "functional" impression, a precise topological or "functional" model, and an occlusion mold or bite impression, all, in some cases, leading to the creation of a final denture, plate or other dental or orthodontic appliance. However, the step(s) in which impressions in trays are used to produce plaster casts are those processes with which the present product and method are concerned.

A consequence of the inevitable design of impression trays used to make lower teeth impressions is that a large space or void exists where the tray is contoured for receiving a patient's tongue during an impression step. If left unoccluded, this void will fill with plaster during the casting process-plaster which must later be painstakingly removed to acquire adequate access and visualization of the teeth in the resulting plaster model.

Some dental and orthodontic offices use alginate (the same material that is used as the actual impression) to fill this void in the lower impression tray and, thereby, partially avoid the excess plaster problem. This is not an efficient or cost-effective solution to the problem. Alginate is not forgiving of mixing errors, often sets up more quickly than is consistent with its use after an impression is taken and to fill the void in the lower teeth tray for casting, and is somewhat expensive. Other dental and orthodontic offices simply do nothing, and, after a plaster model is made, carefully trim away the excess plaster to gain access and visualization to the pertinent portions of the model. This latter approach is extremely time-consuming and even poses a potential health risk due to the dust produced by the plaster removal process. This can also lead to having to make a totally new model due to plaster buildup and problems encountered during trimming the model, which is a waster of time and expense. Sometimes this involves calling the patient back into the dental office for a new impression.

Another, separate problem which arises in the context of making dental models relates to unintended gaps or voids in the plaster model which is produced as part of the progression to a final dental appliance. When plaster models are produced, inevitably there are gaps and voids formed by bubbles, air pockets, molding technique mistakes, etc. In addition, certain gaps which are accurate reflections of the patient's mouth or dental structures will be filled when making the plaster model for the ultimate production of dental appliances—missing natural teeth, for example. Such gaps or voids must be filled and properly contoured before using the model for further development of a dental appliance. Otherwise, a new model must be made—a considerable waste of time and expense, and one sometimes involving calling the patient back into the dental office for a new impression.

U.S. Pat. No. 6,786,722, incorporated herein in its entirety by reference, teaches a method and a related product which can be used to solve many of the problems discussed above and to avoid the excess plaster problems inherent in the use of lower teeth impression trays. The product is a dough-like filler material. Its commercialized embodiment is a product known in the dental and orthodontics industry as Wonderfill®. The method and the dough-like filler material are simple to use, very cost-effective, environmentally benign, and at least as effective as any known method or product. The dough-like filler material is used (in lieu of more expensive, less easily handled filler materials) in the process of making plaster dental molds for dental or orthodontic use to fill voids in dental impression molds, voids which otherwise would allow for the formation of obstructive plaster accumulations in the resulting plaster dental mold. In addition, the method and the dough-like filler material can be used to quickly, conveniently, and cost-effectively fill voids (caused by bubbles, air pockets, etc.) in plaster models, in order to avoid having either to replace the defective models or to consume expensive materials which are difficult to work with in this context.

U.S. Pat. No. 7,083,413, incorporated herein in its entirety by reference, teaches an improved method for producing dental models through use of the dough-like filler material taught in U.S. Pat. No. 6,786,722 as a base. This method comprises the steps of: forming a user-formed base of moldable, dough-like material; embedding a dental preliminary impression in a surface of this material; embedding a mold ring member into the same surface, in a position to encircle the preliminary impression within the bounds of the mold ring member; inserting dental model casting material atop the user-formed base and the preliminary dental impression; after curing of the casting material, removing the mold ring member from the combined casting material, preliminary impression, and user-formed base; and removing the user-formed base and preliminary impression from the cured dental casting material.

A comprehensive search of patents and patent applications published since 2002 was performed to determine what "updates" may have occurred in the relevant technological field concerning orthodontic modeling filler materials and related methods since the filing of the applications that led to the issuance of U.S. Pat. Nos. 6,786,722 and 7,083,413. It was found that the patent applications that were filed, and the patents that were issued, were primarily concerned with various polymeric/elastomeric/composite compositions that are used for the initial taking of the dental impressions with dental trays, and they are not concerned with the casting part of the process. Thus, these patent documents regarding various impression compositions and materials are not directly relevant since they don't specifically address the use of filler materials during the casting process. It appears, therefore, that the type of dough-like filler material used in the casting process described in U.S. Pat. Nos. 6,786,722 and 7,083,413 has not been the subject of any further development documented in the patent literature since the filing of the applications that led to the issuance of these two patents.

While the dough-like filler material and its method of use, as taught by U.S. Pat. Nos. 6,786,722 and 7,083,413, have been used extensively by dental and orthodontic practitioners for many years, the technology as taught therein did suffer from certain shortcomings: (1) The cooking step used during the manufacturing process of the dough-like filler material left a lot of room for human error. Everything had to happen at a very precise time, with human intervention being required for the process to work correctly. For example, when cooking on the grill, flipping had to happen at precisely 4:00 minutes or the product would begin to melt from cooking too long. If the worker took too long to flip the product, then one side of the product would burn or melt. Kneading had to happen for at least 1:30 minutes or the product would become too gooey and would not be cooked thoroughly. If the employee's arms got tired and they stopped kneading too soon the product would not turn out with an appealing consistency. Moreover, the temperatures of each heating element had to be taken and recorded between each batch to ensure the oven was not too hot where the product would melt instead of cook. (2) The quality of the manufactured product varied somewhat from batch to batch for unknown reasons despite the same manufacturing steps being used for each batch of product. Some batches of the product would not setup properly in the cooling stage and would become very gooey and sticky. (3) Some batches of the product were not lasting as long as desired on the shelf. Such batches were turning orange within a few months of production, while a shelf life of at least one year (12 months) was desired.

In summary: (1) the dough-like filler material of U.S. Pat. Nos. 6,786,722 and 7,083,413 that has been sold under the trademark WONDERFILL® has proven useful to dental and orthodontic practitioners; (2) none of the developments in the relevant technological fields since the issuance of the above-numbered patents have resulted in products that could replace this dough-like filler material; and (3) the technology taught in U.S. Pat. No. 6,786,722 for manufacturing the dough-like product suffers from certain shortcomings summarized above. Improvements of this technology that yield consistently high quality batches of filler material product and that extend the shelf life of that product would, therefore, be highly beneficial.

SUMMARY OF THE INVENTION

In view of the foregoing, it is an object of the present invention to provide an improved dough-like filler material that is more consistent and is not gooey or sticky and has an extended shelf life. In some embodiments the improved filler material comprises, by percent volume, 36.5% to 39.5% standard baking flour, 18.5% to 19.5% salt, 30% to 35% distilled water, 4% to 5% cream of tartar, 4% to 5% vegetable cooking oil, and 0.4% to 0.7% aromatic oil. The improved dough-like filler material after processing is for use with dental model impression trays in occluding space which is otherwise filled with excess plaster during a plaster model casting process, but it is not subject to the shortcomings of the dough-like filler material taught in U.S. Pat. Nos. 6,786,722 and 7,083,413.

The inventors have also discovered that using dry weights for all non-liquid ingredients (the "dry ingredients") during initial mixing of the filler material, rather than using volume measurements for the dry ingredients, results in a more efficient process and can be adjusted such that less of each dry ingredient is used to achieve a more desirable end-product. Thus, in a preferred embodiment, the ingredients by percent weight/percent mass of total ingredients added to the product mixture throughout the entire manufacturing process of the filler material are 23% to 30% flour, 23% to 29% salt, 4% to 6% Cream of Tartar, 33% to 41% distilled water, 4% to 6% vegetable oil, and 0.4% to 0.7% aromatic oil. The best mode of this preferred embodiment found by the inventors for a 40 oz. (1134 grams) unit of prepared filler material product involves mixing approximately 335 grams flour, 330 grams salt, 60 grams cream of tartar, 470 grams distilled water, 60 grams vegetable oil, and 7 grams of peppermint oil. This best mode results in an approximate 11% reduction of flour, 15% reduction of salt, and 15% reduction of water when compared to the "recipe" previously disclosed in the specification of the U.S. Pat. No. 6,786,722, and this is even after accounting for the difference between the 51 oz. unit size taught in that patent and the 40 oz unit size discussed herein.

In a preferred embodiment of the invention, the aromatic oil is peppermint oil, which is used for multiple purposes in the dough-like filler material. Peppermint oil, also known as *Mentha piperita* L., is a medicinally important plant that belongs to the Family Lamiaceae. It is a hybrid of *M. spicata* L. (spearmint) and *Mentha aquatic*. Peppermint oil is an essential oil extracted from the aerial parts of the flowering plant, the dried leaves, the fresh flowering plant and the whole plant. Peppermint oil has been shown to have antibacterial, antiviral, and antifungal properties, and has an aromatic odor that is thought to be pleasant by many people. One aspect of the invention hereby disclosed is the recognition after much testing that the addition of a much greater amount of aromatic oil, which is peppermint in the preferred embodiment, yields a better, more consistent dough-like filler material that has a longer shelf-life than the prior WONDERFILL® product.

The constituents further include food coloring in some embodiments.

It is another object of the present invention to provide an improved method for manufacturing the dough-like filler material, said method comprising the steps of: (a) mixing the flour, salt, water, cream of tartar, cooking oil, and optional food coloring constituents of said material to form a mixture possessing substantially uniform consistency and texture; (b) cooking said mixture at an elevated, evenly-distributed temperature; (c) adding aromatic oil to the cooked mixture and kneading; (d) packaging in a specified product weight per container for storage and/or shipment; and (e) performing all of the above steps at a constant low humidity.

In a preferred embodiment of the manufacturing method, the initial filler material mixture is heated at an evenly-distributed temperature that is precisely maintained in the range of 130° C. to 140° C. Such heating occurs for a duration in the range of 6 minutes to 10 minutes, depending on the embodiment. In practice, a high quality pizza oven may be used to provide the even heating required to appropriately cook the improved dough-like filler material. The use of a pizza oven for the cooking step is a major improvement over the prior method that incorporated a grill.

Another significant improvement over the prior method involves use of distilled water that is heated to exactly 100° F., and not lower than that temperature, prior to use. This is discussed in greater detail herein.

Cooling is performed in stainless-steel baking pans that sit on the racks of a cooling shelf in some embodiments. This method of cooling provides additional advantages, as discussed herein.

It is another object of the invention to provide a method for producing and finishing a plaster dental model, this method comprising the steps of: (a) making a dental impression for use of an impression material-filled impression tray, the impression tray having a void for accommodating a patient's tongue; (b) applying a plaster material to the dental impression for producing a plaster dental mold; and (c) upon curing of the plaster dental model, filling undesirable voids in the plaster dental model with the improved dough-like filler material.

The improved dough-like filler material of the present invention is a drop-in replacement, providing the benefits of savings of time and money, for the dough-like filler material of U.S. Pat. Nos. 6,786,722 and 7,083,413 in all of its dental and orthodontic applications.

BRIEF DESCRIPTION OF THE DRAWINGS

The disclosed invention will be described with reference to the accompanying drawings, which show important sample embodiments, wherein.

DETAILED DESCRIPTION OF THE PREFERRED EMBODIMENTS

Figure 1:
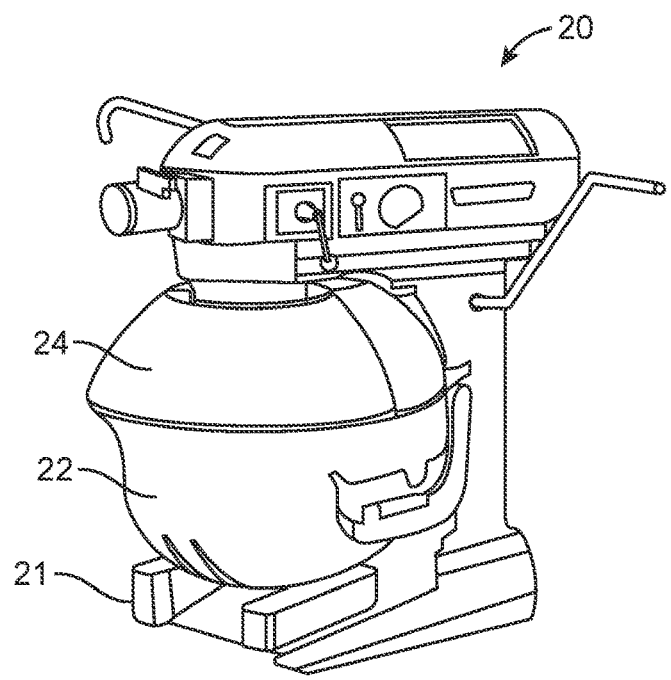
FIG. 1 is a front-side perspective view of an industrial mixer in its entirety with a lid on the mixing bowl.

An exemplary "recipe" for a finished 40 oz. (1134 grams) unit of product according to one embodiment of the improved dough-like filler material based on volume measurements of ingredients used throughout the manufacturing process is provided in Table 1 below. Similar batches of any other desired quantity can be manufactured by using the volume percentages listed in Table 1 of each ingredient and using equipment of size and capacity suitable for processing the batches of other desired quantities. For instance, in actual practice the inventors prepare the filler material in 320 oz. batches, and thus the batches that are prepared actually use eight times the volumes per ingredient that are shown in Table 1 below. Volumes of ingredients provided in Table 1 may range by ±10%.

TABLE 1

An exemplary 40 oz. (1134 grams) unitized "recipe" for an embodiment of the dough-like filler. A standard 320 oz. batch would require eight times as much ingredients.

| Ingredient | Volume of Ingredient | Volume Percent |
| --- | --- | --- |
| Standard Baking Flour | 2.353 cups | 38.4 |
| Salt | 1.176 cups | 19.2 |
| Cream of Tartar (Potassium Bitartrate) | 4.706 tbsp | 4.8 |
| Water | 1.997 cups | 32.6 |
| Vegetable Oil | 4.444 tbsp | 4.5 |
| Peppermint Oil | 8.215 mL | 0.5 |

An exemplary 40 oz. (1134 grams) unitized "recipe" for a preferred embodiment of the improved dough-like filler material based on weight/mass measurements is provided in Table 2 below. Similar batches of any other desired quantity can be manufactured according to the preferred embodiment by using the weight/mass percentages listed in Table 2 of each ingredient and using equipment of size and capacity suitable for processing the batches of other desired quantities. As stated above, the inventors typically manufacture the filler material in 320 oz. batches that result in eight 40 oz. units of finished product at the end of the manufacturing process, so the ingredients shown in Table 2 below would be multiplied by a factor of eight in order to arrive at the actual amounts per ingredient used in the real-life manufacturing process. Weight/mass of ingredients provided in Table 2 may range by ±10%.

TABLE 2

An exemplary 40 oz. (1134 grams) unitized "recipe" for the preferred embodiment of the dough-like filler material. A standard. 320 oz. batch would require eight times as much ingredients as shown.

| Ingredient | Weight/Mass Added | Weight/Mass Percent |
|---|---|---|
| Standard Baking Flour | 335 grams | 26.5 |
| Salt | 329 grams | 26.1 |
| Cream of Tartar (Potassium Bitartrate) | 59 grams | 4.7 |
| Water | 471 grams | 37.4 |
| Vegetable Oil | 61 grams | 4.8 |
| Peppermint Oil | 7 grams | 0.5 |

It should be noted that during the manufacturing process some of the water that is part of the initial mixture of ingredients will be lost or "cooked off" during the heating/cooking step. This is the primary reason why the total weight/mass of all the constituent ingredients required to make a 40 oz unit of filler material as shown in Table 2 above is greater than the final weight/mass of the prepared filler material per 40 oz. (1134 grams) unit. Furthermore, it should also be understood that the peppermint oil listed in the two tables above is not added during the initial mixing phase of the manufacturing process, but rather, the peppermint oil is added during the kneading step that occurs after the heating/cooking step.

The precise method of manufacture of the present filler material is, as mentioned before, the result of much additional experimentation and adjustment. The process, in its preferred embodiment (for making one 40 oz. (1134 grams) unit (but scalable for larger batches, such as the commonly prepared 320 oz. batch) is as follows:

Mixing

The starting ingredients incorporated into the formulation during the initial mixing step of the process are listed in Table 3 below. Peppermint oil is not included during this step. It is added during the subsequent kneading step to obtain the final (complete) recipe listed in Table 2 above.

TABLE 3

Starting ingredients incorporated into the formulation during the initial mixing step of preparation of the preferred embodiment of an exemplary 40 oz. (1134 grams) unitized amount of the improved dough-like filler material. Actual batches during production are typically 320 oz. in total amount at the end of the manufacturing process and prior to packaging.

| Ingredient | Amount |
|---|---|
| Distilled Water (warmed to exactly 100° F.) | 1.997 cups (479 mL) Liquid Volume |
| Vegetable Oil | 4.444 tbsp. (66 mL) Liquid Volume |
| Food Coloring (optional) | 56 drops (3 mL) Liquid Volume |
| Standard Baking Flour | 11.804 oz. (335 grams) Dry Weight/Mass |
| Salt | 11.608 oz. (329 grams) Dry Weight/Mass |
| Cream of Tartar (Potassium Bitartrate) | 2.086 oz. (59 grams) Dry Weight/Mass |

Figure 2:
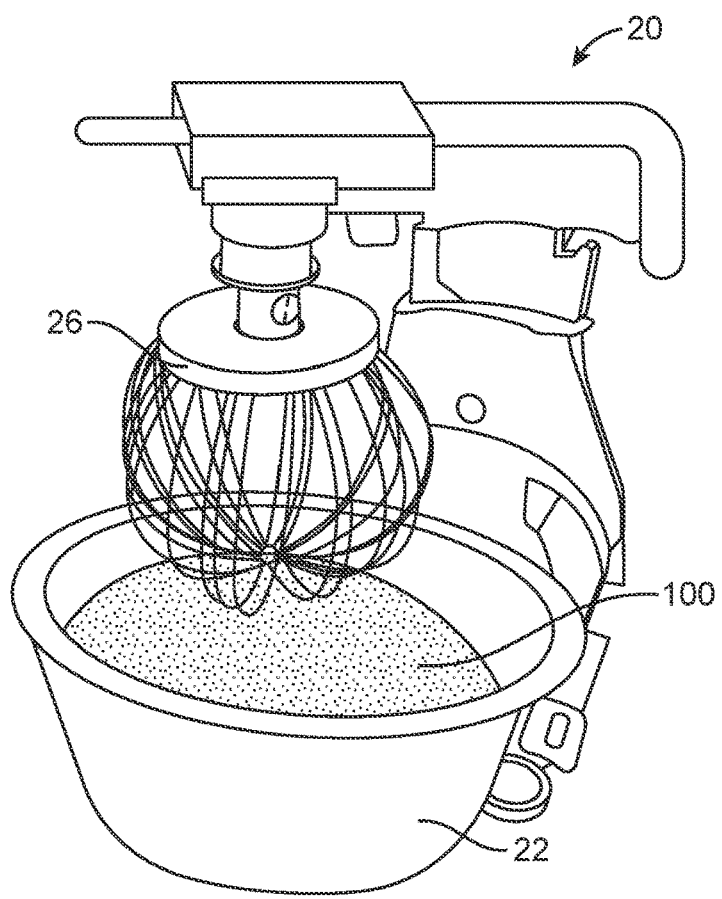
FIG. 2 is a front-side perspective view of the industrial mixer with the lid open showing the interior filled with the initial mixture that will become the dough-like filler material.
Figure 3:
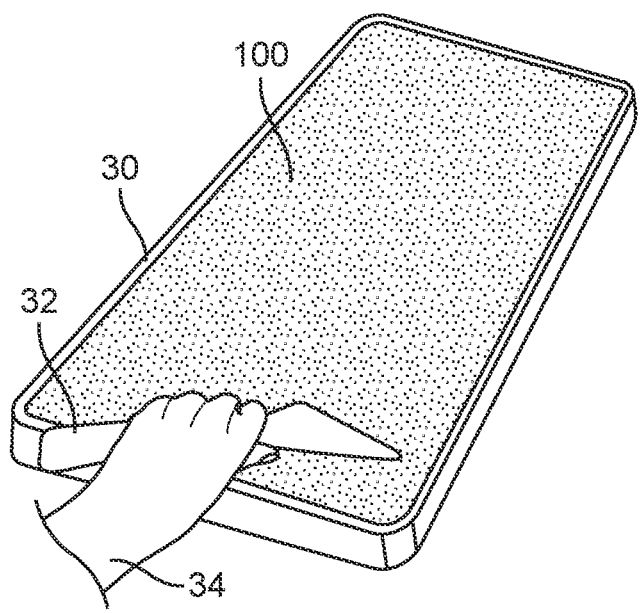
FIG. 3 is a perspective view of a baking pan containing a batch of the initial mixture after the completion of the mixing step of the manufacturing process.

The mixing step of the manufacturing process is illustrated, in part, in FIGS. 1-3. The mixing step of the manufacturing process is comprised of the following sub-steps in one embodiment of the manufacturing process:

1. Heat distilled water to exactly 100° F. (heated to 100° F. (37.8° C.), not substantially hotter or cooler).
2. Measure the vegetable oil and the warm distilled water to be used.
3. Add the warm distilled water (100° F.) to a mixing bowl 22 appropriate to the size of the intended batch, as shown in FIG. 1.
4. Pour the food coloring into the mixing bowl 22 with the warm water (optional). Stir the water and food coloring mixture thoroughly.
5. Add all dry ingredients slowly into the mixing bowl 22 and then hand stir completely.
6. Add the vegetable oil to the mixing bowl 22.
7. As shown in FIG. 1-2, place the mixing bowl 22 onto a commercial mixer stand 21 of a commercial mixer 20 (preferably a mixer with at least three speeds, such as a HOBART Model A200, is exemplary for this method), attach a spiral whisk tool 26 to the mixer 20, and latch mixing bowl 22 on both sides. Attach a lid 24 to the top of the mixing bowl 22.
8. Set a timer for 30 seconds and mix ingredients using the mixer 20 set at its lowest speed.
9. Turn the mixer 20 up to a higher, medium speed, and mix for an additional minute.
10. Reset the timer for 1 minute and mix on the next highest speed of the mixer 20 (third speed on a mixer with three or more speeds).
11. Stop the mixer 20 and the timer. The initial mixture of the filler material 100 is now ready for further processing.
12. As shown in FIG. 3, pour the initial mixture of the filler material 100 from the mixing bowl 22 of the mixer 20 into a baking pan 30 and use a plastic spatula 32 to spread the initial mixture of the filler material 100 in the pan 30 and to scrape the excess from the baking pan 30. FIG. 3 shows a baking pan 30 containing the initial mixture of the filler material 100 after the completion of the mixing step of the process.

*Total mixing time: 2 minutes and 30 seconds.

Heating/Cooking

Figure 4:
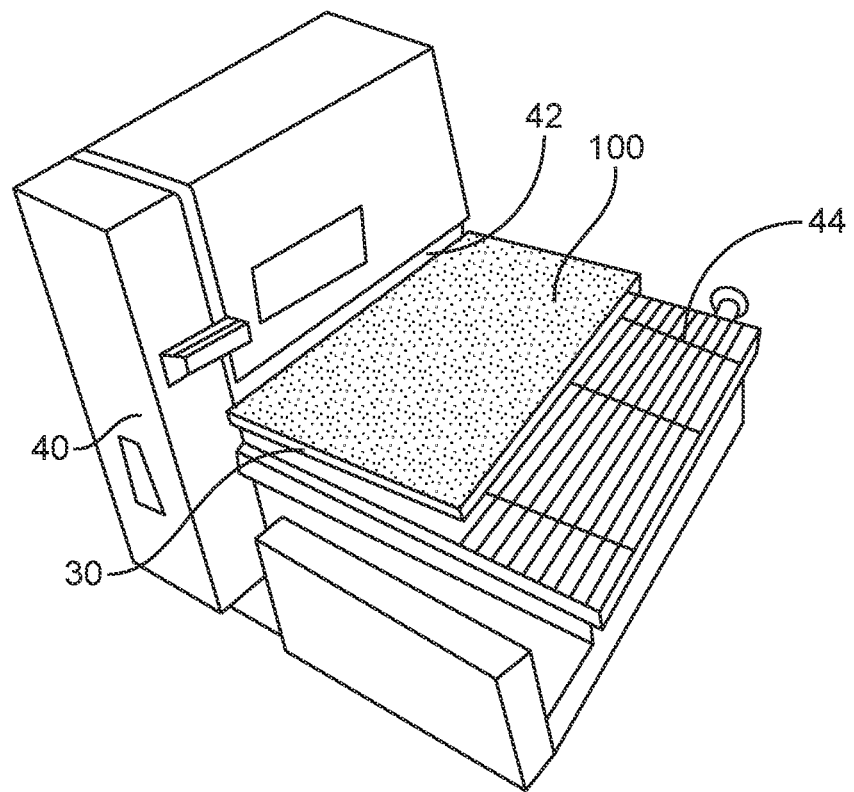
FIG. 4 is a top perspective view that shows a batch of the material mixture in a baking pan while it is coming out of a pizza oven on a conveyor after heating.

The Heating/Cooking Step of the manufacturing process is illustrated in FIG. 4. The Heating/Cooking Step of the manufacturing process is comprised of the following sub-steps in one embodiment of the process:

1. Set the baking pan 30 containing the initial mixture of the filler material 100 onto an oven conveyor 44, parallel with the edge of the oven opening 42.
2. Have the conveyor 44 take the baking pan inside an oven that will provide evenly-distributed heat at a selected temperature, such as a pizza oven 40 (for example, a Lincoln 1100 Series Impinger® II Conveyorized Oven).
3. Cook the initial mixture of the filler material 100 at an evenly-distributed 270° F.-275° F. (132° C.-135° C.) for 8 minutes inside the pizza oven 40. For example, the use of a conveyorized pizza oven 40 results in even heat distribution, stable temperature, and less moisture being released (thereby preventing the product from becoming sticky and soft and as a result preventing the completed filler material from easily releasing from the model after the setup time for the plaster/stone to dry).
4. Remove the baking pan 30 from the conveyor 44 after it comes out of the oven 40. FIG. 4 shows a cooked mixture of the filler material 100 on a baking pan 30 coming out of a pizza oven 40.

The cooking temperature and duration do not need to be varied over wide ranges as a function of humidity, and are in fact quite insensitive to humidity, since the heating/cooking step in the manufacturing process involves heating the initial mixture of the filler material evenly with an even distribution of heat being maintained within an oven by the heating element. This may be accomplished with the use of a pizza oven 40 as opposed to the grill top (Star-Max Electric Griddle Model 548TGF) that was used in the prior art approach taught in U.S. Pat. No. 6,786,722, and such even heat distribution during the heating/cooking step is a major improvement over the prior art process. Another advantage of the use of a conveyorized pizza oven 40 over the use of a grill top is the simplification of the cooking process, resulting in the reduction of human errors that may lead to product of poor quality. The identification of a pizza oven 40 as a better tool than a grill top for use during cooking was a surprising result of many experiments performed while searching for an improved heating/cooking process.

Kneading and Cooling

Figure 5:
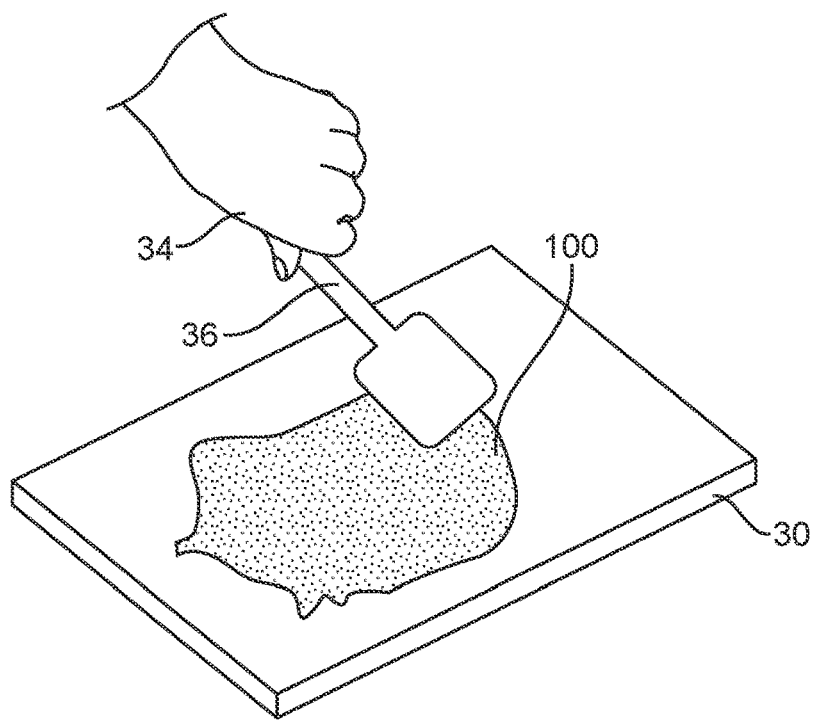
FIG. 5 is a perspective view of a balling step of the process wherein a spatula is used to fold the product into a large ball.
Figure 6:
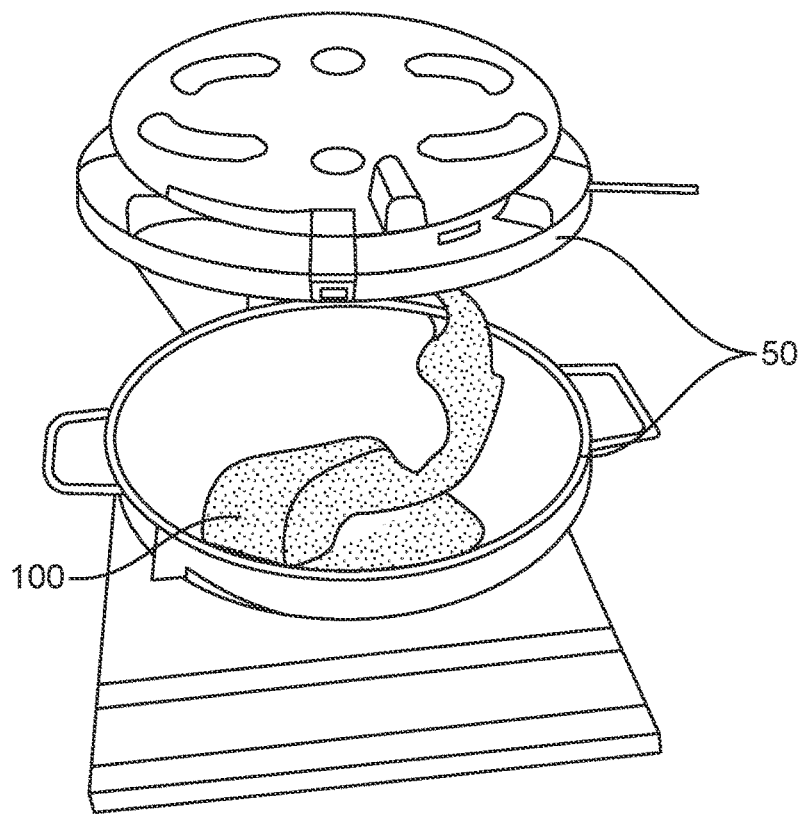
FIG. 6 is a top perspective view of the kneading step of the manufacturing process wherein the ball of mixed, cooked material is picked up and dropped into a kneading bowl of a kneading machine that will be used to accomplish the kneading step.
Figure 7:
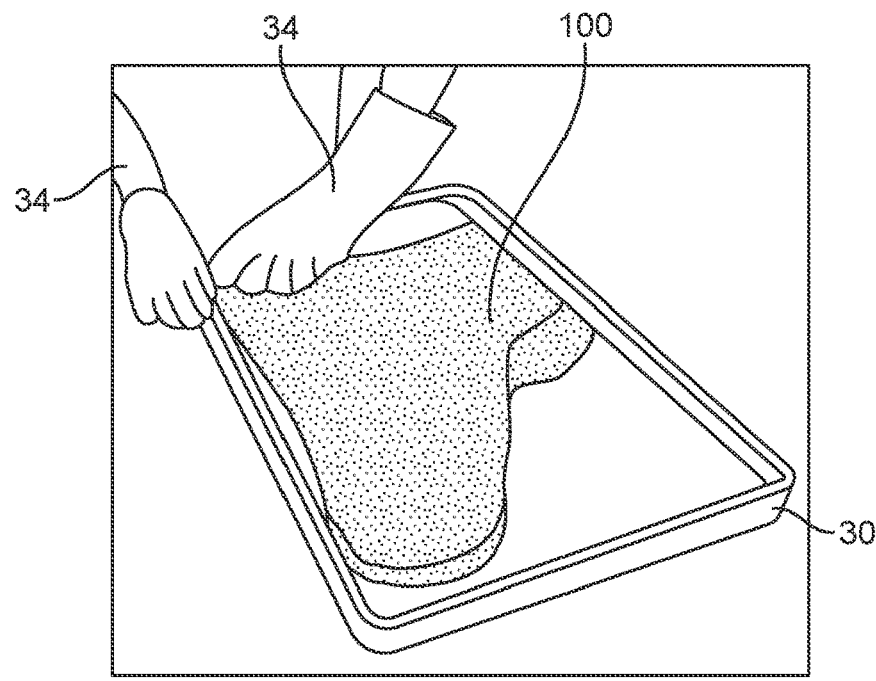
FIG. 7 is a perspective view of the product after being removed from the kneading bowl and spread evenly on a baking pan to cool.
Figure 8:
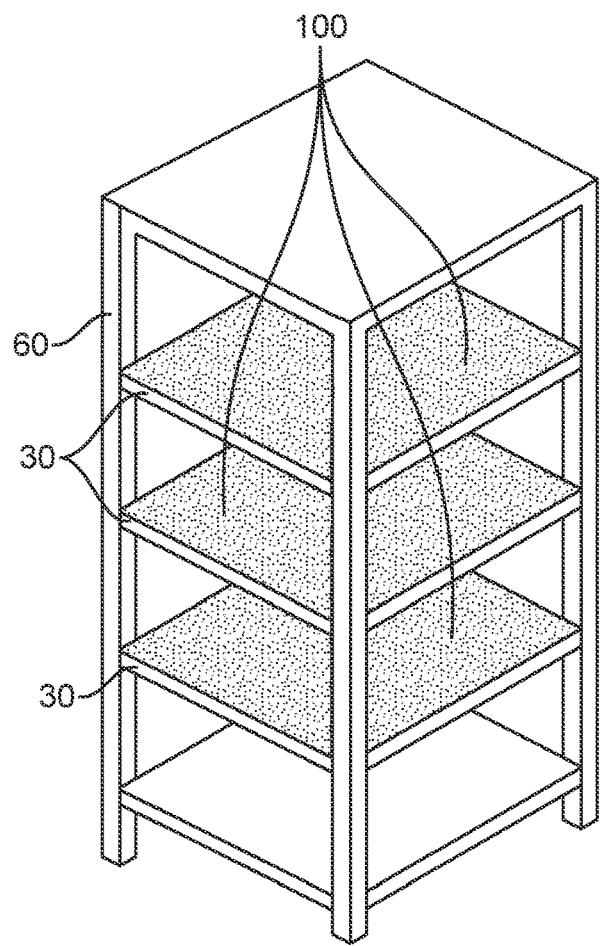
FIG. 8 is a perspective view of multiple batches of the kneaded product after being spread evenly on baking pans, and those baking pans having been placed on cooling racks of a cooling shelf.

The Kneading and Cooling Steps of the manufacturing process are illustrated in FIGS. 5-8. The Kneading and Cooling Steps of the manufacturing process are comprised of the following sub-steps in one embodiment of the process:

1. Use a spatula 36 to fold the intermediate filler material 100 into a large ball. This sub-step is illustrated in FIG. 5.
2. As shown in FIG. 6, pick up the ball of intermediate filler material 100 and drop it in the kneading bowl 49 of a kneading machine 50 (a HOBART Model D330 kneading machine is exemplary for the present method). Attach a hook paddle style beater (not illustrated) to the kneading machine 50, and latch kneading bowl 49 on both sides.
3. Add approximately 7.5 mL of peppermint oil.
4. Raise the kneading bowl 49, close the guard 48, start the kneader 50, and knead the intermediate filler material 100 for approximately 45 seconds on an intermediate speed (such as speed 2 on the HOBART Model D330 kneading machine).
5. Remove the intermediate filler material 100 from the kneading bowl 49 and spread it evenly in a baking pan 30. This sub-step is illustrated in FIG. 7.
6. Once the intermediate filler material 100 is evenly distributed in the baking pan 30, the pan 30 is placed on of a multiplicity of cooling racks 30 of a cooling shelf 60 where it will cool for a minimum of 2.5 hours-3 hours, or at least until the middle of the filler material product 100 is cooled to approximately room temperature (74° F.). This sub-step is shown in FIG. 8.

The filler material product 100 dries out if it cools for too long. The filler material product 100 "sweats" and becomes sticky and gooey if it does not cool long enough. The prior art version of the product was cooled on a plastic table for 24 hours before the manufacturing process was improved. The new method of cooling the product in large stainless-steel baking pans that sit on a rack of a cooling shelf allows the product to cool completely in 2.5 hours to 3 hours. In practice, multiple baking pans containing the filler material product may be set on the cooling racks of one or more cooling shelves for cooling at the same time. Because the filler material product cools so quickly and thoroughly, there is no worry of the product either becoming too dry or sweating.

Packaging

The product should not be packaged while it is still hot. As discussed above, it is important to let the filler material product cool to room temperature (74° F.) in baking pans placed on cooling racks of one or more cooling shelves prior to packaging.

Figure 9:
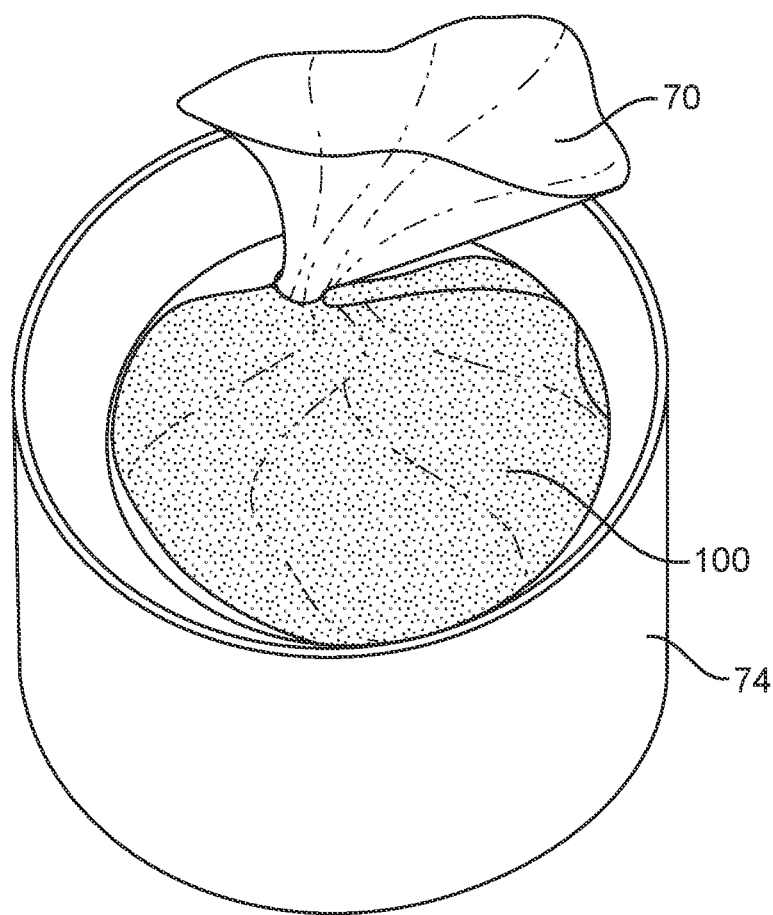
FIG. 9 is a perspective view of the cooled dough-like filler material product being packed into buckets with plastic liners for storage and/or shipment.

As shown in FIG. 9, the old packaging step can be as simple as weighing out 40 oz. (1134) unit sizes of the filler material 100 using a scale, wiping it down with a small amount of cooking spray (such as PAM® cooking spray) and then bagging that unitized 40 oz. amount in a plastic bag 70 that is pressed down to remove air. In this simple packaging step, the plastic bag 70 containing 40 oz. of the filler material product 100 is then placed into a container 74 for storage and/or shipment to customers. Thus, this simple version of the packaging step that is illustrated by FIG. 9 is essentially the same as the packaging step previously disclosed in U.S. Pat. No. 6,786,722. This type of packaging step could still be employed in the current manufacturing process, but in actual practice it has been supplanted by the newer method discussed below.

Figure 10:
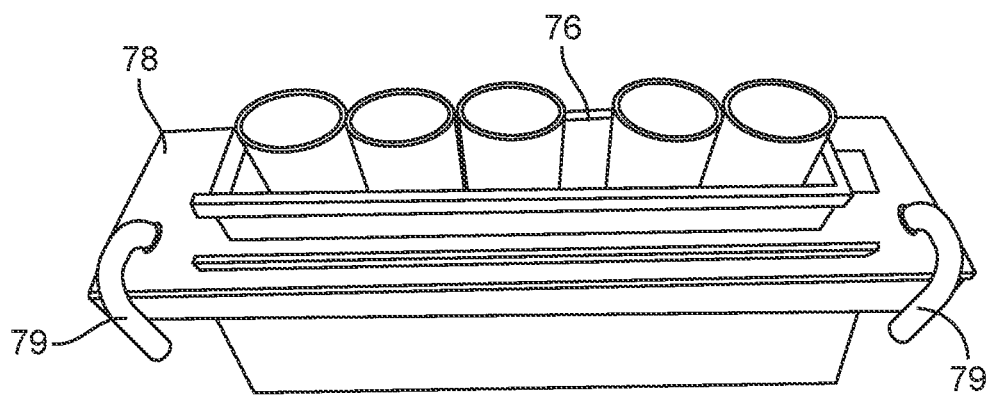
FIG. 10 is a perspective view of a packing jig that has been clamped to the packing table by using 2 large C-clamps.
Figure 11:
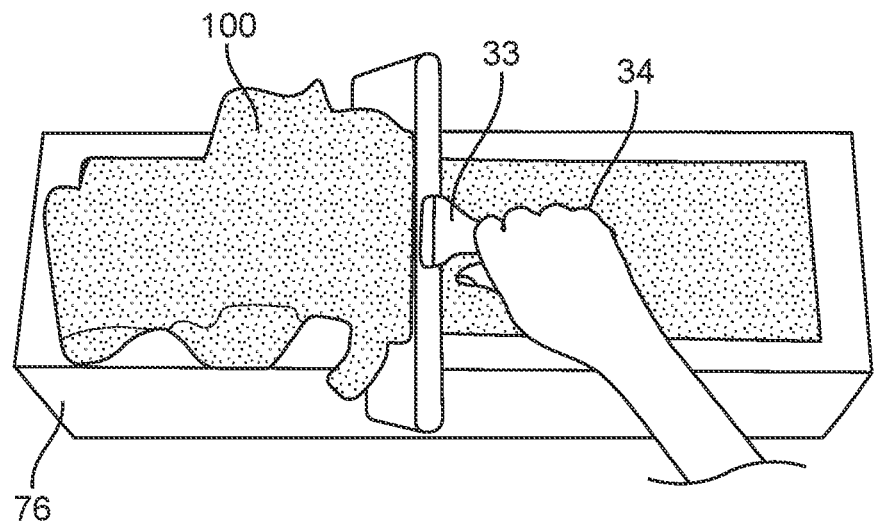
FIG. 11 is a perspective view of the removal of excess product from the top of the packing jig by using a flat knife or similar tool.
Figure 12:
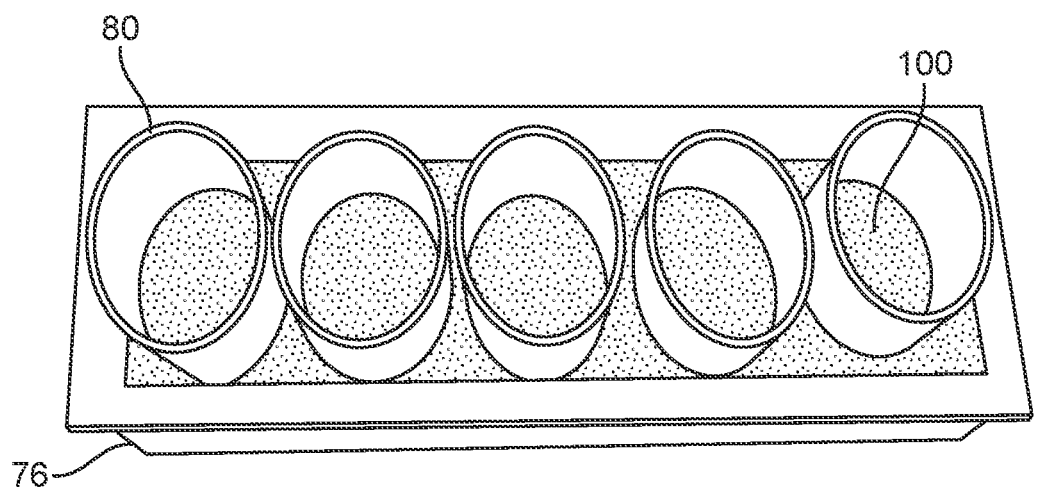
FIG. 12 is a perspective view that shows the pressing of five PVC pipe cutouts into the product in the packing jig.
Figure 13:
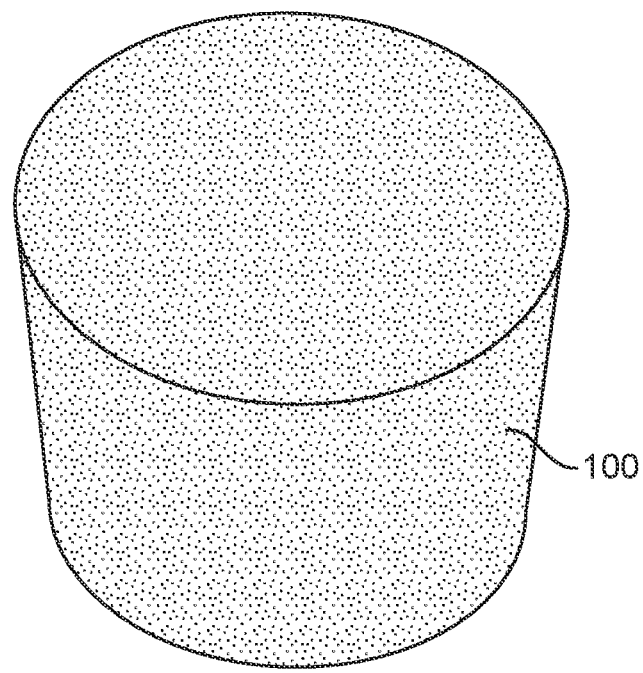
FIG. 13 is a perspective view of the product after it has been released from one of the five PVC cutouts.
Figure 14:
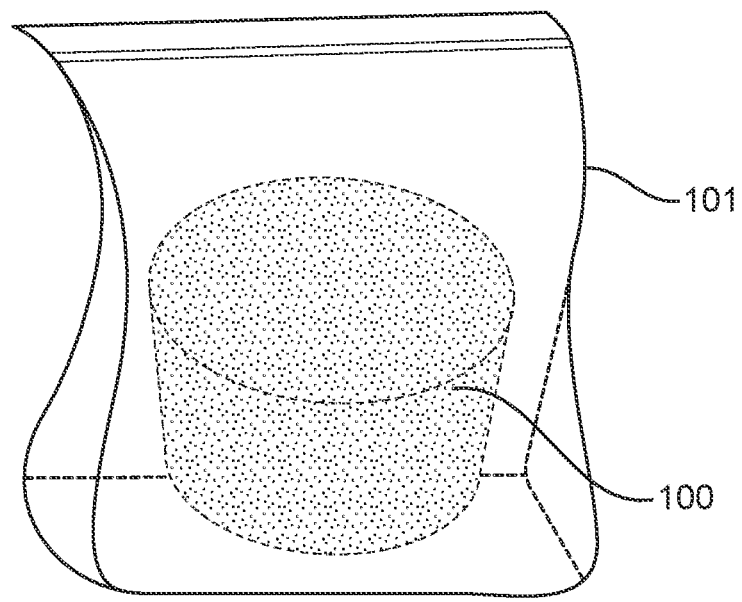
FIG. 14 is a perspective view that shows the product after it has been placed inside a plastic bag for storage and/or shipment.

The inventors have recently devised an improved packaging step that is more efficient and less time-consuming than the previous simple packaging step shown if FIG. 9 that was previously disclosed in U.S. Pat. No. 6,786,722. As illustrated in FIGS. 10-14, the improved packaging step includes the following sub-steps that may be performed in certain embodiments of the manufacturing process, but only after the product has cooled down on the cooling rack of a cooling shelf:

1. As shown in FIG. 10, clamp a packing jig 76 to a packing table 78 by using two large C-clamps 79.
2. As shown in FIG. 11, fill the packing jig 76 completely with the filler material 100 and pack the filler material 100 in tightly within the packing jig 76.
3. Remove excess filler material product 100 from the top of the packing jig 76 by using a flat knife 33 so that no excess remains above the top edges of the packing jig 76.
4. As shown in FIG. 12, press five PVC pipe cutouts 80 into the filler material product 100 that is within the packing jig 76. As demonstrated in FIG. 10, the PVC cutouts 80 are longer than the depth of the packing jig 76, so the tops of the PVC cutouts will stick up above the top of the packing jig 76 when they are fully inserted into the filler material 100 that is contained within the packing jig 76.
5. Remove the packing jig 76 from the packing table 78 by loosening and removing the C-clamps 79 and then lifting the packing jig 76 off the packing table 78.
6. Remove all excess from outside of the PVC pipe cutouts 80 and then release the finished, unitized filler material product 100 from the five PVC cutouts 80 so that what is left over after removal from each cutout 80 is a 40 oz. unit of finished filler material product 100 as shown in FIG. 13.
7. Spray a foam sponge lightly with a vegetable oil cooking spray (such as PAM® brand cooking spray) and wipe the top and edges of the finished filler material product 100 with sponge. The vegetable oil cooking spray can also be sprayed onto another surface, such as a lid for a container 74, and then the sponge can be lightly brushed against that surface and then used to apply a small amount of the vegetable oil to the outside of the filler material 100.
8. As shown in FIG. 14, place the finished filler material product 100 in a plastic bag 101, press down to remove air, and close the bag 101.
9. Place the bagged product into a container 74 such as the one shown in FIG. 9.

The filler material product will become dry and crumbly if it sits out too long. One unit of the product was packaged at a given time when the previous, prior art manufacturing process was used (as illustrated in FIG. 9). This left a lot of extra product sitting out on the table for extended periods of time waiting to be packaged. The new packaging process illustrated in FIGS. 10-14 includes using the packing jig 76 and multiple cutouts 80 which allows the manufacturer to cut and package five units of the product at a given time. Doing so improves the packaging speed by a factor of five and eliminates any concerns about the product sitting out having enough time to dry out before it gets cut and packaged.

There are a number of additional aspects to the new manufacturing process and the new filler material product that are not obvious from a review of FIGS. 1-14 or the above detailed description of the steps of the new, improved manufacturing process. These aspects of the new manufacturing process will now be discussed in the paragraphs below.

Importantly, the entire manufacturing process is now performed in a humidity-controlled environment wherein the relative humidity is maintained within a range of 30% to 36% humidity. Other than the time the filler material is cooking in the oven, this precise humidity range is maintained throughout the entirety of the manufacturing process by the use of multiple dehumidifiers and because all steps of the process are performed within a room that is insulated with an open-cell spray foam. The precise range of humidity is maintained during the initial mixing step, the heating/cooking step, the kneading and cooling step, and the product packaging step. This humidity range is maintained inside the oven with humidity sensors when the material is heated/cooked at an evenly-distributed, elevated temperature. Production is shut down if the relative humidity exceeds 36% during any step in the process because higher humidity causes the product to become both too sticky and too soft. This set humidity range during manufacturing is an important innovation because it results in increased density of the product which makes the product perform far better than the previously-patented version of the filler material because the improved filler material exhibits no sticking to the plaster/stone model, the product is significantly easier to mold, and the product cleans out easier after use thereby decreasing the risk of having to pour the model again.

The completed, finished, and packaged product is typically stored in a cold room. The cold room used for the storage of the product temperature storage is set to a temperature of 62° F.-66° F. (16.7° C.-18.9° C.). Storage in a cold room with the temperature maintained within this range extends the shelf-life of the product and prevents the product from releasing oil and prevents it from turning yellow or orange after long periods of storage. If significantly colder temperatures are used, the product tends to sweat, release oil, and turn yellow after significant time in storage. However, if significantly warmer temperatures are used, the product dries out and becomes crusty and salty at the top after significant time in storage.

Another difference between the current invention and the prior art that was disclosed in U.S. Pat. Nos. 6,786,722 and 7,083,413 is that the prior art used unpurified water (such as tap water) in formulating the product, while distilled water is used in the present invention. The inventors have found, unexpectedly, that the replacement of tap water with distilled water results in higher product quality and yield as a result of the elimination of the tendency towards caking. Without being bound by theory, the inventors think that the reason for the significant improvement in product quality and yield when distilled water is used instead of tap water arise from the fact that distilled water does not contain any impurities that can disrupt the action of the cream of tartar (potassium bitartrate) that is being used as an anti-caking (leavening) agent. By contrast, tap water can contain many impurities and chemicals that can disrupt the anti-caking effect of cream of tartar, and furthermore the concentrations of these impurities and chemicals can vary from day to day to add to the inconsistencies in quality and yield. The use of distilled water eliminates these fluctuations and provides for better control, and thus a more consistent product.

In addition, the new manufacturing process and improved filler material thereby created involve a significant increase in the amount of aromatic oil (in a preferred embodiment the aromatic oil is peppermint oil) that is used. For instance, the amount of peppermint oil used as an ingredient in the embodiments shown in both Tables 1 and 2 above represent an over 1,200% increase in the amount of peppermint oil that is used in the filler material as compared to the amount previously disclosed in the specification of U.S. Pat. No. 6,786,722. A benefit of the use of a much larger quantity of peppermint oil (or other aromatic oil) in the present invention, which was a surprising result of experimental work targeting the manufacturing of a product with an extended shelf life, is that the product becomes far more durable. More specifically, while the shelf life of the product manufactured according to prior art was about six months maximum, the shelf life of the product manufactured according to the present invention is now longer than one year.

It should also be noted that peppermint oil is only one of many examples of aromatic oils that may potentially be used as a preservative in embodiments of the filler material and the process of manufacturing such material. The use of another aromatic oil which is also demonstrated to be capable of serving as a preservative is also within the scope of the invention. Furthermore, while peppermint oil in an amount that is at least 1,200% more than the amount that was previously used in the prior art filler material is part of the preferred embodiment of the improved filler material, it has also been found that adding a small amount of lemon oil may result in a more buoyant/more pliable and fluffy resulting filler material product.

It should be understood that variations in constituents, such as moisture in flour, ambient temperature in the manufacturing facility, water quality, etc. may require slight variations in cooking, kneading, and cooling times, as well as slight adjustments in relative volumes of constituents. However, such variations will be within the skills of any competent batch manufacturing supervisor or manager. Therefore, the quantities and the cooking, kneading, and cooling times, while found to be optimal in working conditions of relatively normal range of temperature and humidity, and using constituents of standard quality (14% moisture in standard baking flour, for example), should, in other conditions or circumstances, be understood to be approximate. If adjusting cooking times for a minute one way or the other, or, for example, varying constituent amounts by a relative or so, should be required to meet other than standard conditions or circumstances to produce product of desirable characteristics, such should be understood to still fall within the scope of the present invention.

It is further anticipated by the inventors that the amounts of ingredients used in the embodiments of the improved filler material as shown in Tables 2 and 3 above could range within about a ±10% range and yet still fall within the scope of the invention hereby disclosed. The amounts specified in the Tables 2 and 3 represent a preferred embodiment and also the best mode of the invention discovered by the inventors to date, but it should be understood that a variance in the ingredients by up to 10% more or 10% less would still fall within the scope of the invention.

Use of the Improved Filler Material

Figure 15:
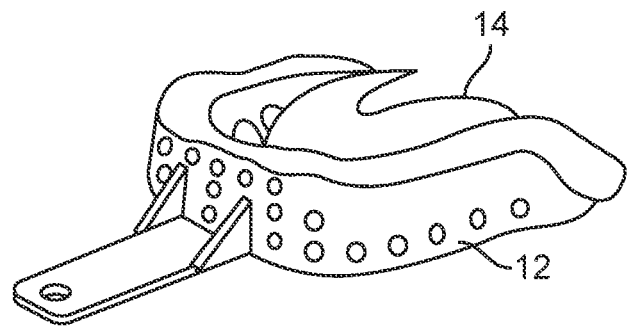
FIG. 15 is a perspective view of a dental impression tray prior to application of any of the improved filler material of the present invention.

Referring to FIG. 15, after an initial impression is taken, and impression tray 12 will include a void 14 where a patients tongue resided during the impression process.

Figure 16:
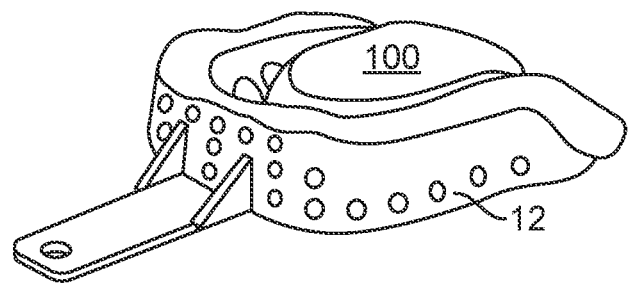
FIG. 16 is a perspective view of the impression tray shown previously in FIG. 15, but this time with the filler material of the present invention applied to occlude the void otherwise present after the impression step.

Referring to FIG. 16, the present improved filler material 100 is, according to the present invention, manually placed and formed to occlude the void 14. The filler material 100, properly manufactured according to the present invention, will remain in place after applying light pressure, but will not stick to one's hands under most circumstances. Once the filler material 100 is in-place, the plaster casting step of dental modeling follows according to conventional processes.

Figure 17:
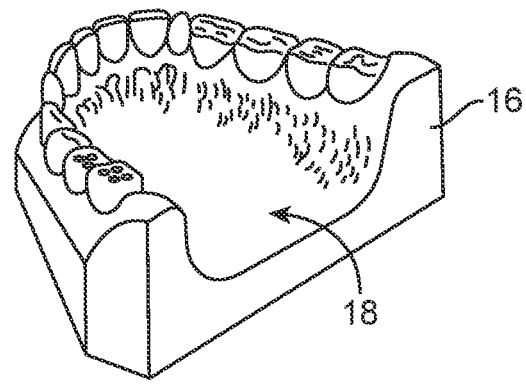
FIG. 17 is a perspective view of a plaster cast model showing a cavity left by the presence of the improved filler material during the plaster casting process, a cavity that would otherwise be filled with plaster had such a filler material not been used.

Referring to FIG. 17, a plaster model 16 is depicted and shows a large cavity 18. Cavity 18 is the result of the improved filler material 100 having resided in void 14 of tray 12 during the plaster casting process. Had filler material 100 not been positioned as described, excess and obstructive plaster material would have occupied cavity 18 and prevented ready access and visualization of the interior surfaces of the teeth renditions of the plaster model 16.

Although not referenced in FIGS. 15-17, the use of the subject improved filler material to fill voids in plaster dental models is an independently significant aspect of the present invention. Once a plaster dental model is created, if voids or holes are present, these must be filled and contoured to match that which the model should have replicated, but for the air gap or bubble which created the void or hole during the molding process. As with the use of the present filler material in lieu of alternative dental modeling materials which might otherwise be used to fill such voids, use of the present filler material to fill voids and holes in plaster dental models will save practitioners' time and money to a very significant degree. Use of alginate and the like in this context poses the same problems and objections as in using it to fill the tongue void in a lower dental impression as discussed above.

The use of the improved filler material 100 in the described contexts obviates a number of problems as already described. Filler material 100 is either substantially odor free or pleasantly scented. Once mixed, and if kept in any sealed container, filler 100 exhibits a very long shelf life, if the distilled water and peppermint oil (or like material) is used during the manufacturing process. Whether used to fill a cavity 18, or to fill gaps or voids, or to create structures where none existed (missing teeth), use of the filler material 100 renders the resulting models 16 more useful and accurate than models made without the use of such a void occluding material, and without excessive lab technician contouring and carving time.

It should also be noted that the PVC cutouts discussed in the packaging step above and shown in FIG. 10 and FIG. 12 do not necessarily have to be made from PVC pipe and do not have to be open cylinders. The cutouts used to package multiple portions of the dough-like filler material may be open volumetric forms of essentially any shape that are made from a relatively rigid material. The inventors have generally employed cutouts of PVC pipe in large enough diameter to internally accommodate dough-like filler material in a volume that results in approximately 40 oz. units that can be placed into individual containers for storage or shipment. However, it is clear that open volumetric forms with cubical, hexagonal, octagonal, or other shapes could be used for the same purpose and in the same manner to more or less separate the dough-like filler material in the packing jig into separate unitized amounts for placement into containers. Likewise, the packing jig has been illustrated in FIG. 10-FIG. 12 as being a rectangular or cubical open-faced trough, but the shape of the packing jig may vary and need not be rectangular or cubical so long as it can be temporarily clamped on top of a surface and filled with the dough-like filler material and then released so that the individual cutouts containing portions of the filler material may be easily accessed and excess material removed from the outside of the cutouts prior to placing the unitized portions into separate containers.

The improved dough-like filler material of the present invention is a drop-in replacement, providing the benefits of savings of time and money, for the dough-like filler material of U.S. Pat. Nos. 6,786,722 and 7,083,413 in all of its dental and orthodontic applications.

Although the invention has been described with reference to specific embodiments, this description is not meant to be construed in a limiting sense. Various modifications of the disclosed embodiments, as well as alternative embodiments of the invention, will be apparent to persons skilled in the art upon reference to the description of the invention. It is, therefore, contemplated that the appended claims will cover such modifications that fall within the scope of the invention.

We claim:

1. A method for producing and finishing a plaster dental model comprising the steps of:
   making a dental impression using an impression material-filled impression tray, said impression tray having a void for accommodating a patient's tongue;
   occluding said void with a dough-like filler material that is made by the following steps:
      mixing together the following ingredients:
         300-370 grams flour;
         295-360 grams salt;
         53-65 grams cream of tartar;
         55-67 grams cooking oil;
         424-518 grams water;
      spreading the mixed ingredients on a pan and cooking the ingredients at 130° C. to 140° C. for 6 minutes to 10 minutes;
      kneading the ingredients together with 7.4 mL to 9 mL of aromatic oil to form an intermediate material;
      spreading the intermediate material onto a pan and setting that pan on a cooling rack to cool for at least 2.5 hours so as to become the completed dough-like filler material;
   packaging the dough-like filler material in one or more containers.

2. The method of claim 1 wherein the water is distilled prior to use.

3. The method of claim 1 wherein the cooking is done within an oven that distributes heat evenly within the oven.

4. The method of claim 1 wherein the packaging step is accomplished using a packing jig such that:
   the packing jig is filled to its top with the dough-like filler material;
   multiple open volumetric forms are inserted into the dough-like filler material within the packing jig so that portions of the dough-like filler material will be located within at least a part of the internal volume of the volumetric forms;

the packing jig is removed;

excess dough-like filler material is removed from the outside of the volumetric forms;

the portions of the dough-like filler material contained within the volumetric forms are released from the volumetric forms and are then respectively packaged in individual containers.

\* \* \* \* \*